United States Patent
Winkler (10) Patent No.: US 6,537,194 B1
(45) Date of Patent: *Mar. 25, 2003

(54) CATHETER WITH PERMEABLE HYDROGEL MEMBRANE

(75) Inventor: Rance A. Winkler, Atlanta, GA (US)

(73) Assignee: Proxima Therapeutics, Inc., Alpharetta, GA (US)

( * ) Notice: Subject to any disclaimer, the term of this patent is extended or adjusted under 35 U.S.C. 154(b) by 11 days.

This patent is subject to a terminal disclaimer.

(21) Appl. No.: 09/724,121

(22) Filed: Nov. 28, 2000

Related U.S. Application Data (63) Continuation of application No. 09/275,910, filed on Mar. 24, 1999, now Pat. No. 6,200,257.

(51) Int. Cl.[7] ................................................ A61N 5/00
(52) U.S. Cl. ............................................................ 600/3
(58) Field of Search .............................. 600/3, 4, 435, 600/470; 128/898; 604/509, 265, 266

(56) References Cited

U.S. PATENT DOCUMENTS

| | | | |
|---|---|---|---|
| 3,630,200 A | 12/1971 | Higuchi | 424/427 |
| 4,950,256 A * | 8/1990 | Luther et al. | 604/265 |
| 5,258,042 A | 11/1993 | Mehta | 623/66 |
| 5,458,568 A | 10/1995 | Racchini et al. | 604/19 |
| 5,509,899 A | 4/1996 | Fan et al. | 604/96 |
| 5,628,730 A | 5/1997 | Shapland et al. | 604/21 |
| 5,634,901 A | 6/1997 | Alba et al. | 604/96 |
| 5,674,192 A | 10/1997 | Sahatjian et al. | 604/28 |
| 5,693,034 A | 12/1997 | Buscemi et al. | 604/265 |
| 5,709,653 A | 1/1998 | Leone | 604/20 |
| 5,833,682 A | 11/1998 | Amplatz et al. | 606/15 |
| 5,843,156 A | 12/1998 | Slepoan et al. | 128/898 |
| 5,954,706 A | 9/1999 | Sahatjian | 604/509 |
| 6,200,257 B1 * | 3/2001 | Winkler | 600/3 |

* cited by examiner

Primary Examiner—Max F. Hindenburg
Assistant Examiner—Brian Szmal
(74) Attorney, Agent, or Firm—Thomas J. Engellenner; Geoffrey S. Smith; Nutter McClennen & Fish LLP (57) ABSTRACT

Drug delivery vehicles and catheter systems are disclosed for controlled release of therapeutic agents employing a permeable hydrogel membranes a reservoir for an inflation fluid carrying a therapeutic agent. The membrane devices of the present invention can be used in conjunction with a catheter or similar instrument having an elongated hollow body member and a lumen extending therethrough to permit fluid communication between a proximal infusion port and a permeable membrane disposed at the distal end of the catheter body. The membrane preferably comprises an expandable, hydrophilic polymer having a predetermined permeability with respect to an inflation fluid. One preferred hydrophilic polymer is a hydrogel capable of imbibing an aqueous solution to reach a state in which it comprises between 50% and 98% water by weight in equilibrium. In this state, the hydrogel membrane serves to control the rate of medicament delivery.

13 Claims, 3 Drawing Sheets

CATHETER WITH PERMEABLE HYDROGEL MEMBRANE

This is a continuation application of U.S. Ser. No. 09/275,910, filed on Mar. 24, 1999, now U.S. Pat. No. 6,200,257, the contents of which are incorporated in their entirety.

FIELD OF THE INVENTION

This invention relates generally to medical devices for delivering therapeutic agents to selected tissue site through a hydrophilic membrane. More particularly the invention relates to catheter systems that have injection ports for delivery of therapeutic fluids and a membrane attached to a distal portion of the catheter into which the fluid is delivered, thereby inflating the balloon. The membrane is formed from a hydrophilic polymer that exhibits a predetermined permeability such that therapeutic solutions delivered through the injection port(s) into the membrane are contacted directly, which are in contact with the inflated membrane.

BACKGROUND OF THE INVENTION

Various forms of drug delivery catheters are known in the art. They generally comprise an elongated flexible catheter body having an inflatable member at a distal end portion thereof where the inflatable member or "balloon" has pores formed in the wall thereof through which a drug containing fluid can profuse. For example, U.S. Pat. No. 5,709,653 to Leone uses a balloon catheter with a porous balloon for allowing a photodynamic treatment fluid to pass through the pores and infuse into the wall of a body vessel in which the catheter is disposed. Other patents utilizing a porous balloon for drug delivery include Racchini et al. U.S. Pat. No. 5,458,568; Sahatjian et al. U.S. Pat. No. 5,674,192 and Shapland et al. U.S. Pat. No. 5,628,730.

Unfortunately, porous balloons are difficult to manufacture (requiring precision drilling of an elastic material) and the minimum practical pore size is often much larger than desired. Moreover, the typical porous balloon system of the prior art has an undesirable release profile, characterized by rapid initial release of a drug or other agent followed by an exponential drop-off as the balloon deflates and the fluid pressure driving the agent through the pores becomes smaller and smaller.

Accordingly, there exists a need for better drug delivery systems and, in particular, delivery systems with greater control over release rates. Balloon or other membrane-based drug delivery systems that can selectively pass molecules at a controlled and reproducible rate would satisfy a long-felt need in the art.

SUMMARY OF THE INVENTION

The present invention circumvents the problems described above by delivering a therapeutic agent, e.g., a medicament, into an area in need thereof, via a membrane that permits greater control of the application and release rates of the medicament. In a particular embodiment, the invention provides a device, which allows chemotherapeutic or radiosensitized treatment of a particular diseased tissue area with minimal if any exposure of non-diseased tissue to the treatment. Drug delivery vehicles and catheter systems of the invention are disclosed for controlled release of therapeutic agents, e.g., medicaments such as chemotherapeutic agents or radiosensitizers, employing a permeable hydrogel matrix, e.g., a membrane, and a reservoir for an inflation fluid carrying a therapeutic agent.

The devices of the present invention can be used in conjunction with a catheter or similar instrument having an elongated hollow body member and a lumen extending therethrough to permit fluid communication between a proximal infusion port and a permeable membrane disposed at the distal end of the catheter body. The device preferably comprises an expandable, hydrophilic polymer membrane, e.g., a hydrogel membrane, e.g., a balloon, having a predetermined permeability with respect to an inflation fluid. One preferred hydrophilic polymer is a hydrogel capable of imbibing an aqueous solution to reach a state in which it comprises between 50% and 98% water by weight in equilibrium. In this state, the hydrogel membrane serves to control the rate of medicament delivery.

By injecting an inflation fluid comprising an aqueous solution containing a medicament, the membrane member can be inflated to engage body tissue (e.g., the interior surface of a blood vessel or other body lumen or tissue surrounding a natural or excised interstitial space within the body). The membrane can engage the body tissue over a substantial portion of its length and simultaneously exude the inflation fluid containing the medicament through the membrane so as to bathe the engaged tissue and surrounding tissues, e.g., a vessel wall, with the drug or other therapeutic substance.

The invention is also drawn to methods for treating aberrant cells or cancer in a body cavity. The methods include inserting a catheter including an elongated tubular body member into a body cavity, the tubular body having a proximal end, a distal end and a lumen extending therebetween, with an inflation port extending through a wall of the tubular body member in fluid communication with the lumen. An expandable membrane member is affixed to the catheter body member near the distal end and in fluid communication with at least one inflation port.

The membrane member includes a hydrophilic polymer having a predetermined permeability to migration of inflation fluid therethrough. An inflation solution containing a medicament is injected into the expandable membrane such that the medicament permeates through the membrane over a period of time treating the aberrant.

In one embodiment, the method further includes slidably positioning an insertion tube with radioactive pellet(s), e.g., seed(s), into a lumen of the catheter, such that ionizing radiation strikes the medicament, preferably a chemotherapeutic agent or a radiosensitizer, thereby treating the aberrant cells with an activated medicament.

In another embodiment, the methods include inflating a second membrane, which is fixedly attached to the catheter and proximate to the first membrane with a solution containing a radioactive isotope. Preferably, the radioactive solution emits ionizing radiation that interacts with a chemotherapeutic agent or a radiosensitizer forming activated molecules useful for treating aberrant cells or cancer.

The invention will next be described in connection with illustrated embodiments. However, it should be clear that various additions, subtractions and substitutions can be made without departing from the spirit or scope of the invention. For example, the membranes of the present invention can be bonded to the catheter in many different ways so long as a fluid pathway exists between an inflation fluid source and the membrane. The membrane can be multi-walled or multi-layered so long as the overall structure has a predefined permeability.

The membrane can be affixed or otherwise joined to the catheter body without the need for defined inflation ports and can also be stored in a collapsed or recessed state prior to use, e.g., an open-ended catheter. The membrane and catheter components can be sold separately and permeable membranes according to the invention can be designed or adapted to connect to various conventional medical instruments. Broadly, the invention encompasses each of the various elements, methods and features described herein alone or in combination with any other element, method or feature.

BRIEF DESCRIPTION OF THE DRAWINGS

The foregoing features, objects and advantages of the invention will become apparent from the following detailed description of illustrative embodiments in conjunction with the accompanying drawings in which like reference numerals designate like parts throughout the figures thereof and wherein.

DETAILED DESCRIPTION OF THE ILLUSTRATED EMBODIMENTS

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

In one aspect, the present invention pertains to a biocompatible drug delivery catheter that includes an elongated tubular body member and an expandable biocompatible membrane member affixed to the catheter body. The elongated tubular body member has a proximal end, a distal end and a lumen extending therebetween, with at least one inflation port extending through a wall of the tubular body member. In a preferred embodiment of the invention, the inflation port(s) is in fluid communication with the lumen. In one embodiment the inflation port can be the open end of the catheter where the membrane is affixed to the end of the catheter and acts as a capping feature.

The expandable membrane member, e.g., a biocompatible membrane balloon, is affixed to the catheter body member near the distal end and is in fluid communication with at least one of the inflation ports. The membrane member consists of a hydrophilic polymer having a predetermined permeability for migration of inflation fluid therethrough. Upon injection of an inflation fluid, e.g., a pharmaceutically acceptable carrier and a medicament, the expandable membrane inflates forming a "reservoir" between the catheter body and the outerwall of the membrane.

Figure 1A:
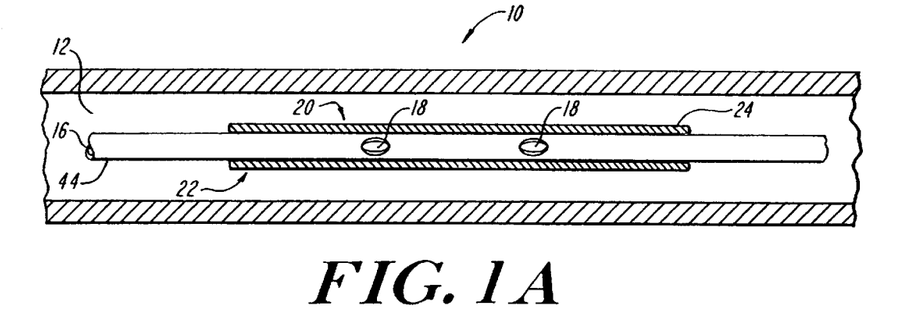
FIG. 1A is a cross-sectional view of the distal end portion of a drug delivery device constructed in accordance with the present invention and contained within a tubular body lumen in an uninflated state.
Figure 1B:
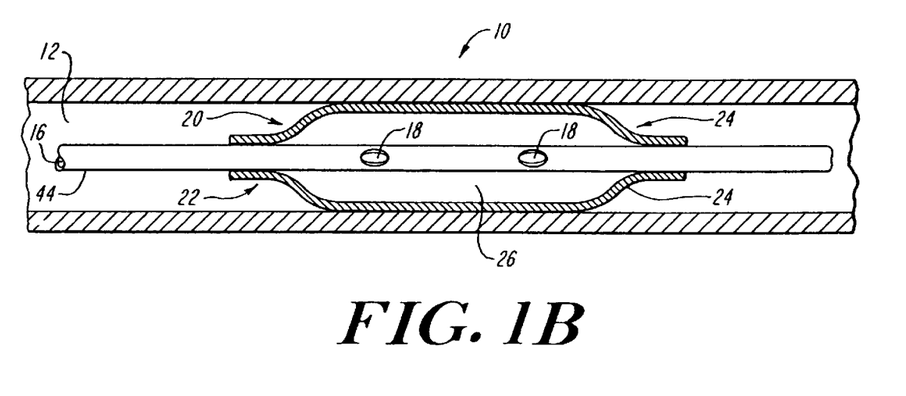
FIG. 1B is another cross-sectional view of the device of FIG. 1A following inflation of the membrane.

In FIGS. 1A and 1B a drug delivery catheter 10, constructed in accordance with the present invention, is depicted in its unexpanded and expanded form within a body cavity such as a lumen of a blood vessel 12. The catheter 10 is somewhat conventional in its construction in that it includes an elongated flexible tubular body 14 having at least one lumen 16 extending the length thereof from a proximal end to a distal end. Openings in the side wall of the body member 14 define one or more inflation ports 18 that provide fluid communication between the lumen 16 and an outer membrane 20, which can be bonded at its proximal end 22 and distal end 24 to the tubular body 14. As shown in FIG. 1B, injecting an inflation fluid into the proximal end of the catheter body 14, it is forced to flow through the lumen 16 and out the inflation ports 18 to fill the chamber 26 within the membrane 20, thereby inflating outer membrane 20. Generally the inflation fluid includes a therapeutic agent, e.g., a medicament, which is a chemotherapeutic agent or a radiosensitizer. In a preferred embodiment, the membrane is a hydrogel and is hydrophilic.

By injecting an inflation fluid comprising an aqueous solution containing a medicament, membrane member 20 can be inflated to engage body tissue (e.g., the interior surface of a blood vessel or other body lumen or tissue surrounding a natural or excised interstitial space within the body). Membrane 20 can engage the body tissue over a substantial portion of its length and simultaneously exude the inflation fluid containing the medicament through the membrane so as to bathe the engaged tissue and surrounding tissues, e.g., a vessel wall, with the drug or other therapeutic substance.

"Interstitial cavity," as the term is used herein, encompasses interstices in a tissue or structure of a natural body structure, spaces and gaps existing between layers of tissue or existing within organs, and can include interstices within the interior of the ureter, bladder, intestines, stomach, esophagus, trachea, lung, blood vessel or other organ or body cavity, and will be further understood to include any surgically created interstice that defines an interior cavity surrounded by tissue.

The term "catheter" as used herein is intended to encompass any hollow instrument capable of penetrating body tissue and providing a conduit for a fluid to an inflatable membrane with controlled permeability, including without limitation, venous and arterial conduits of various sizes and shapes, endoscopes, cystoscopes, culpascopes, colonscopes, trocars and laparoscope. Catheters of the present invention can be constructed with biocompatible materials known to those skilled in the art, e.g., silastic, polyethylene, Teflon, polyurethanes, etc.

The terms "into" and "onto" are used interchangeably and are intended to include treatment of tissue by delivering a medicament to the afflicted area. In some instances the medicament penetrates the tissue and in other instances the medicament only superficially treats the surface of the tissue, e.g., contacts or coats. An ordinary skilled artisan would understand what depth(s) of penetration are required and are dependent upon the application, tissue type, area to be treated and severity of condition. Accordingly, the amount of medicament used to treat the afflicted area would be attenuated based upon the disease or condition being treated.

One skilled in the art would recognize those medicaments that would be useful for interstitial treatment of aberrant cell growth, e.g., cancerous tissue (malignant or benign), tumors, etc., by the present invention. The medicaments of interest would include chemicals known in the art which are useful for treating disease states, e.g., cancer, including but not limited to, radiosensitizers and chemotherapeutic agents.

The term "radiosensitizer" is art recognized and is intended to include those agents which, when present during irradiation, enhance the cytotoxic effects of radiation, e.g., ionizing radiation. For example, the hypoxic radiosensitizer Misonidazole, enhances the cytotoxic effect of X-ray and gamma ray radiation. Although studied for many years, the interaction(s) between radiation and a radiosensitizer is complex and difficult to predict. Moreover, as both the radiosensitizer and the radiation are cytotoxic per se, their use in therapy is limited in conventional techniques.

Radiosensitizers are often easily degraded by ionizing radiation into reactive fragments. For example, incorporation of a bromine or iodine atom into DNA using bromodeoxyuridine, e.g., 5'-bromo-2'-deoxyuridine (BUdR) or 5'-iodo-2'-deoxyuridine (IUdR), is known to sensitize DNA to breakage by ionizing or ultraviolet radiation. The sensitization is mediated by the uracilyl free radical formed by dissociation of the carbon-halogen bond in the BUdR or IUdR by UV and the same free radical is formed by a reaction of hydrated electrons produced by ionizing radiation. It has been proposed that the uracilyl free radical initiates strand cleavage by abstraction of the hydrogen atom from the 2'-deoxyribose carbon on the adjacent nucleotide.

The term ionizing radiation is used herein to include photons having enough energy to ionize a bond, such as, alpha ($\alpha$), beta ($\beta$) and gamma ($\gamma$) rays from radioactive nuclei and x-rays.

Various heterocyclic compounds, in particular, those with oxidized nitrogen moieties, have been used for the purpose of radiosensitizing aberrant cells, e.g., tumor cells. Indeed, it has been postulated that the oxidized nitrogen functionality is responsible for this activity. Nitroimidazoles, particularly misonidazole (MIS) and metronidazole have been extensively studied, and MIS is commonly used as a standard in in vitro and in vivo tests for radiosensitizing activity. (See, e.g., Asquith, et al., Radiation Res (1974) 60:108–118; Hall, et al., Brit J Cancer (1978) 37: 567–569; Brown, et al., Radiation Res (1980) 82:171–190; and U.S. Pat. No. 4,371, 540). The radiosensitizing activities of certain 1-substituted 3(5)-nitro-s-triazoles, various quinoxaline-1,4-dioxide derivatives, diamines such as diaminetetrametronidazoles (DATMs) (See for example U.S. Pat. No. 5,700,825), and texaphyrins (See U.S. Pat. No. 5,622,946), for example, have also been disclosed as radiosensitizing agents.

The term "chemotherapeutic agent" is art recognized and is intended to include those chemical and biological agents, including small molecules and larger molecules, such as peptides, proteins, lymphokines, antibodies, tumor necrosis factor, conjugates of antibodies with toxins, and other chemical or biological molecules which have an antitumor effect which is oxygen dependent.

There are a variety of known classes of small molecule chemotherapeutic agents. These include alkylating agents, such as Melphalan (PAM), Cyclophosphamide (CTX), cis-Diammminedichloroplatinum (II) (CDDP), nitrosoureas such as N,N'-bis(II-chloroethyl)-N-nitrosourea (BCNU), nitrogen mustards, ethyleneimine compounds, alkyl sulphonates, cisplatin and dacarbazine. Another general class of antitumor chemotherapeutic agents are the antimetabolites, such as folic acid, purine or pyrimidine antagonists, 6-Mercaptopurine, 5-fluorouracil (5-FU), fluorodeoxyuridine, cytosine arabinoside, methotrexate and thioquinone. Antibiotics are another general class of antitumor chemotherapeutic agents including drugs such as actinomycin, daunorubicin, Adriamycin and bleomycin. Still yet another class are mitotic inhibitors, such as the vinca alkaloids, including etoposide, vincristine and vinblastine and derivatives of podophyllotoxin.

Particular examples of chemotherapeutic agents are described, for instance, by D. J. Stewart in Nausea and Vomiting: Recent Research and Clinical Advances, Eds. J. Kucharczyk et al, CRC Press Inc., Boca Raton, Fla., U.S.A. (1991) pages 177–203. Commonly used chemotherapeutic agents include Adriamycin (doxorubicin), Bleomycin Sulfate, 5-Fluorouracil, Paraplatin (Carboplatin), Methotrexate, Taxol (Paclitaxel), Etoposide, Cytosine Arabinofuraoside (Are-C), Dacarbazine (DTIC), Dactinomycin, Mechlorethamine (nitrogen mustard), Streptozocin, Cyclophosphamide, Carmustine (BCNU), Lomustine (CCNU), Daunorubicin, Procarbazine, Mitomycin, Cytarabine, Etoposide, Methotrexate, 5-fluorouracil, Vinblastine, Vincristine, and Chlorambucil (See, for example, R. J. Gralla et al in Cancer Treatment Reports (1984) 68(1), 163–172).

Mixtures of more than one chemotherapeutic or radiosensitizer agent or combinations thereof can, of course, be administered. Indeed, it is often preferred to use mixtures or sequential administration of different chemotherapeutic or radiosensitizer agents to treat aberrant tissue sites, e.g., tumors, cancerous growths, especially agents from the different classes of agents. For example, mixtures of methotrexate and a cis-platinum compound are often used to treat various afflicted tissue sites.

The term "biocompatible" is art recognized and as used herein, means exhibition of essentially no cytotoxicity while in contact with body fluids or tissues. "Biocompatibility" also includes essentially no interactions with recognition proteins, e.g., naturally occurring antibodies, cell proteins, cells and other components of biological systems.

The terms "treat," "treatment," or "treating" are intended to include both prophylactic and/or therapeutic applications. The methods of the invention can be used prophylatically to protect a subject from damage or injury caused by a disease state or condition, or can be used therapeutically to treat the subject after the onset of the disease or condition.

The term "subject" is intended to include mammals susceptible to diseases, including one or more disease related symptoms. Examples of such subjects include humans, dogs, cats, pigs, cows, horses, rats and mice.

The term "tissue" is art recognized and is intended to include extracorporeal materials, such as organs, e.g., mesentery, liver, kidney, heart, lung, brain, tendon, muscle etc., and corporeal materials, such as blood cells, e.g., red and white blood cells and extracellular components.

The term "disease" is associated with an increase of a pathogen within a subject such that the subject often experiences physiological symptoms which include, but are not limited to, release of toxins, gastritis, inflammation, coma, water retention, weight gain or loss, ischemia and immunodeficiency. The effects often associated with such symptoms include, but are not limited to fever, nausea, diarrhea, weakness, headache and even death. Examples of diseases that can be treated by the present invention include undesirable cell proliferation or cancer, e.g., bladder, urethral, brain mammarian, ovarian cancer, or, ischemia, and benign prostatic hypertrophy or hyperplasia (BHP).

The language "undesirable cell proliferation" is intended to include abnormal growth of cells that can be detrimental to a subject's physiological well being. Effects of undesirable cell proliferation can include the release of toxins into the subject, fever, gastritis, inflammation, nausea, weakness, coma, headache, water retention, weight gain or loss, immunodeficiency, death, etc. The undesired cells that proliferate can include cells that are either benign or malignant. Examples of undesirable cell proliferation include aberrant cell division and/or proliferation of foreign cells, such as in cancer cells.

The terms "aberrant cell" or "aberrant tissues" as used herein, is art recognized and is intended to include aberrant cell division and/or proliferation where cells are generated in excess of what is considered typical in physiologically similar environment, such as in cancers.

The language "control of undesirable cell proliferation" or "controlling undesirable cell proliferation" is intended to include changes in growth or replication of undesired cells or eradication of undesired cells, cancer, or those cells associated with abnormal physiological activity. The language includes preventing survival or inhibiting continued growth and replication of an undesired cell. In one preferred embodiment, the control of the undesired cell is such that an undesired cell is eradicated. In another preferred embodiment, the control is selective such that a particular targeted undesired cell is controlled while other cells which are not detrimental to the mammal are allowed to remain substantially uncontrolled or substantially unaffected, e.g., lymphocytes, red blood cells, white blood cells, platelets, growth factors, etc.

The term "cancer" is art recognized and is intended to include undesirable cell proliferation and/or aberrant cell growth, e.g., proliferation.

The term "modulate" includes effect(s) targeted tissue(s) that prevent or inhibit growth of diseased tissue, which may ultimately affect the physiological well being of the subject, e.g., in the context of the therapeutic methods of the invention.

The term "inflation fluid" is intended to include those solutions, e.g., aqueous solutions, which can be administered to a subject through a device of the present invention without subsequent adverse effects. In general, the inflation fluid is considered a pharmaceutically acceptable carrier or vehicle. The phrase "pharmaceutically acceptable carrier" as used herein means a pharmaceutically acceptable material, composition or vehicle, such as a liquid, diluent, excipient, or solvent, involved in carrying or transporting a medicament useful in the present invention within or to the subject such that it can performs its intended function.

Each carrier must be "acceptable" in the sense of being compatible with the other ingredients of the formulation and not injurious to the patient. Some examples of materials which can serve as pharmaceutically acceptable carriers include excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Besides inert diluents, the inflation fluid can also include adjuvants such as wetting agents, emulsifying and suspending agents, lubricants, such as sodium lauryl sulfate and magnesium stearate, as well as coloring agents, release agents, coating agents, preservative agents and antioxidants can also be present in the compositions.

Examples of pharmaceutically acceptable antioxidants useful in the inflation fluids include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The medicament may conveniently be presented in unit dosage form and may be prepared by any methods well known in the art of pharmacy. The amount of active ingredient that can be combined with a carrier material, e.g., an inflation fluid, to produce a single dosage form will generally be that amount of the medicament that produces a therapeutic effect. Generally, out of one hundred per cent, this amount will range from about 1 percent to about ninety-nine percent of active ingredient, preferably from about 5 percent to about 70 percent, most preferably from about 10 per cent to about 30 percent.

Methods of preparing these formulations include the step of bringing into association a medicament with the carrier and, optionally, one or more accessory ingredients. In general, the formulations are prepared by uniformly and intimately bringing into association a medicament with liquid carriers.

Formulations of the invention suitable for administration may be in a solution or a suspension in an aqueous or non-aqueous liquid, or as an oil-in-water or water-in-oil liquid emulsion, or as an elixir or syrup, each containing a predetermined amount of a medicament as an active ingredient.

Liquid dosage forms for administration of the compounds of the invention include pharmaceutically acceptable emulsions, microemulsions, solutions, suspensions, syrups and elixirs. In addition to the medicinal ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the medicament, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Actual dosage levels of the medicament in the inflation fluids used in conjunction with this invention may be varied so as to obtain an amount of the medicament which is effective to achieve the desired therapeutic response for a particular patient without being toxic to the patient.

The selected dosage level will depend upon a variety of factors including the activity of the particular medicament, the time of administration, the rate of excretion of the particular medicament being employed, the duration of the treatment, other drugs, compounds and/or materials used in combination with the particular medicament employed, the age, sex, weight, condition, general health and prior medical history of the subject being treated, and like factors well known in the medical arts.

A physician or veterinarian having ordinary skill in the art can readily determine and prescribe the effective amount of medicament required. For example, the physician or veterinarian could start doses of the medicament employed in the pharmaceutical composition at levels lower than that required in order to achieve the desired therapeutic effect and gradually increase the dosage until the desired effect is achieved.

In general, a suitable dose of the medicament will be that amount of the medicament that is the lowest dose effective to produce a therapeutic effect. Such an effective dose will generally depend upon the factors described above. Generally, doses of the medicament for a subject, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day.

If desired, the effective daily dose of the medicament may be administered as two, three, four, five, six or more sub-doses administered separately at appropriate intervals throughout the day, optionally, in unit dosage forms.

In accordance with the present invention, the membrane 20 is formed from a hydrophilic polymer exhibiting a predetermined permeability to migration of the inflation fluid through its wall. A suitable hydrophilic polymer is one that will contain between about 50% and about 98% water by weight in equilibrium following imbibition of an inflation fluid and have a permeability coefficient $P \times 10^7$ ($cm^2$ $sec^{-1}$) of at least 150 in its inflated state.

In a preferred embodiment, the membrane permits passage of molecules having molecular weight between about 100 MW to about 85,000 MW, for example between about 100 MW and 500 MW, between about 400 MW and 1000 MW, preferably between about 1000 MW and about 5000 MW, more preferably between about 3000 MW and about 10,000 MW and most preferably between about 25,000 MW and about 85,000 MW. The ranges of molecular weight intermediate to those listed are also intended to be part of this invention, e.g., about 100 to 1000 and about 1000 to about 2000 MW and about 15,000 MW to about 20,000 MW. For example, ranges of molecular weight values using a combination of any of the above values recited as upper and/or lower limits are intended to be included.

In one embodiment, the membrane polymer has an elongation coefficient of at least 1000% upon inflation, preferably at least 500%, more preferably at least 300%, most preferably 200%, such that the membrane matrix swells into a shape which conforms within or to the body cavity and contacts the surrounding tissue, e.g., a balloon, sausage or ball shape. The term "elongation coefficient" is intended to mean that the membrane can expand in any of the x, y, z coordinates to at least 10 times the uninflated dimensions, preferably at least 5 times, more preferably at least 3 times, most preferably at least 2 times its uninflated dimensions without tearing or spilling the contents of the inflation fluid into the body cavity. The elongation coefficient ranges intermediate to those listed are also intended to be part of this invention, e.g., at least about 150% to about 250%, at least about 350% to about 650%. For example, ranges of elongation coefficients using a combination of any of the above values recited as upper and/or lower limits are intended to be included.

The term "hydrophilic" is art recognized and is intended to include those organic and/or inorganic functional groups which are more soluble in water than in nonpolar or hydrocarbon solvents, e.g., water wettable or dissolvable. Suitable examples of hydrophilic polymers include those which have alkoxides, such as phenols, hydroxybiphenyls, polyalkylene oxides (polyethers), polyamines, biphenyls, hydroxylated acrylates and methacrylates, e.g., hydroxylated alkyl acrylates and methacrylates, e.g., hydroxyethyl acrylates, hydroxyethyl methacrylates, hydroxypropylacrylates, hydroxypropylmethacrylates, polyalkylene oxide acrylates and methacrylates and sugar based derivatives, e.g., cellulosics.

The term "hydrogel" is art recognized and is intended to include those polymers that swell with an aqueous solution, e.g., water, between two weight percent and 60 weight percent per volume of gel. Hydrogels are typically 80 to 90% water, preferably between about 50% and 98%, having indices of refraction close to 1.3. Mechanically, the hydrogels should be able to support a breaking tensile stress of between 40,000 and 60,000 dynes/cm2. Chemically, the hydrogels should remain stable and not degrade in vivo. Hydrogel membranes utilized in the present invention can be crosslinked with known crosslinking agents.

The term "membrane" is art recognized and is intended to include those polymeric materials which selectively facilitate the diffusion of small molecules in preference over larger molecules. The membrane can be selected so that molecules of a given molecular weight can pass through the polymeric matrix and molecules with larger molecular weights are retained and do not pass through the polymeric matrix. Preferably the membrane polymeric matrix is a hydrogel.

The membrane polymeric matrix can be crosslinked via those cross-linkers known in the art. For example, di, tri, or tetra acrylates can be used with those monomers listed above to form a crosslinked matrix. Typically, the hydrogel membrane is lightly crosslinked, having a cross-link density of less than 25%, preferably less than 15%, more preferably less than 10%, still more preferably less than 5%, and most preferably less than 2%, e.g., between about 0.1% and 0.5%. The resulting crosslinked membrane still retains the elongation coefficient of expansion as described above. The degrees of cross-link density intermediate to those listed are also intended to be part of this invention, e.g., between about 0.2% and about 0.75%, between about 0.8% to about 1.5% and between about 1.75% to about 2.5%. For example, ranges of cross-link density using a combination of any of the above values recited as upper and/or lower limits are intended to be included.

Membranes are often associated with pore structure, e.g., an effective opening for passage of molecules. In one embodiment, membranes useful in this invention can be considered ultrafiltration membranes. In other embodiments, the pore sizes, in cases where there are distinct pore sizes, range from between about 0.01 microns to about 50 microns, preferably between about 0.02 microns to about 10 microns, more preferably between about 0.05 microns to about 5 microns, most preferably between about 0.1 microns to about 2 microns and between about 0.2 microns to about 2.5 microns. The ranges of pore sizes intermediate to those listed are also intended to be part of this invention, e.g., about 100 to 1000 and about 1000 to about 2000 MW and about 15,000 MW to about 20,000 MW. For example, ranges of molecular weight values using a combination of any of the above values recited as upper and/or lower limits are intended to be included.

Figure 2A:
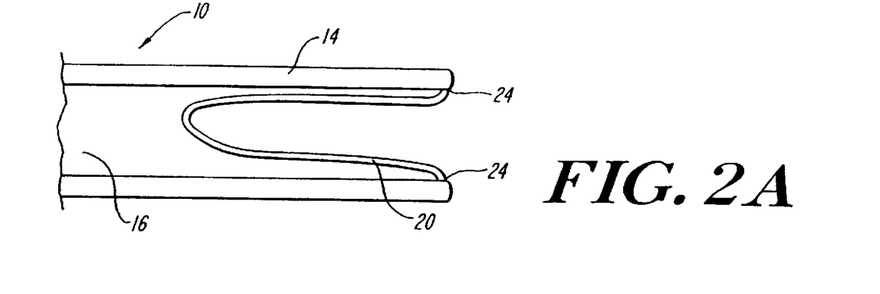
FIG. 2A is a cross-sectional view of another intraluminal device of the invention with the membrane in an uninflated stated and stowed within the lumen of the tubular body.
Figure 2B:
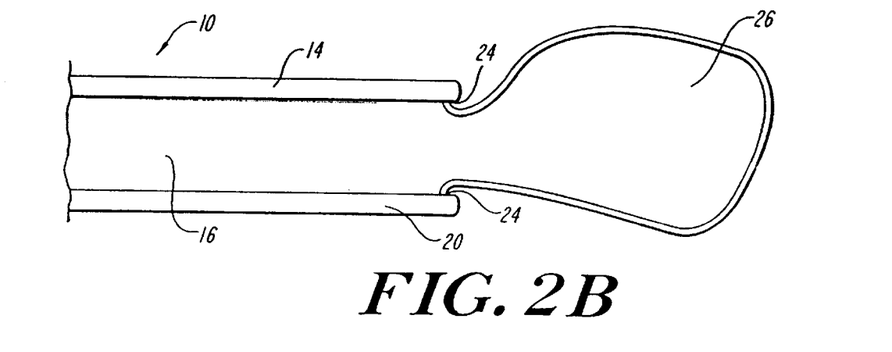
FIG. 2B is a cross-sectional view of a catheter device of FIG. 2A after an inflation fluid has been added through the lumen of the tubular body.

In FIG. 2A, a drug delivery catheter 10, constructed in accordance with the present invention, is depicted in its deflated position. Membrane 20 resides within lumen 16 of tubular body 14 and is fixedly attached at distal end 24. As an inflation fluid is injected through lumen 16, membrane 20 expands outwardly from tubular body 14 as shown in FIG. 2B. The expansion of membrane 20 is dependent upon the length of membrane 20 and the applied pressure of inflation fluid. By this method, membrane 20 can conform to the body cavity to which it is proximate.

Figure 3:
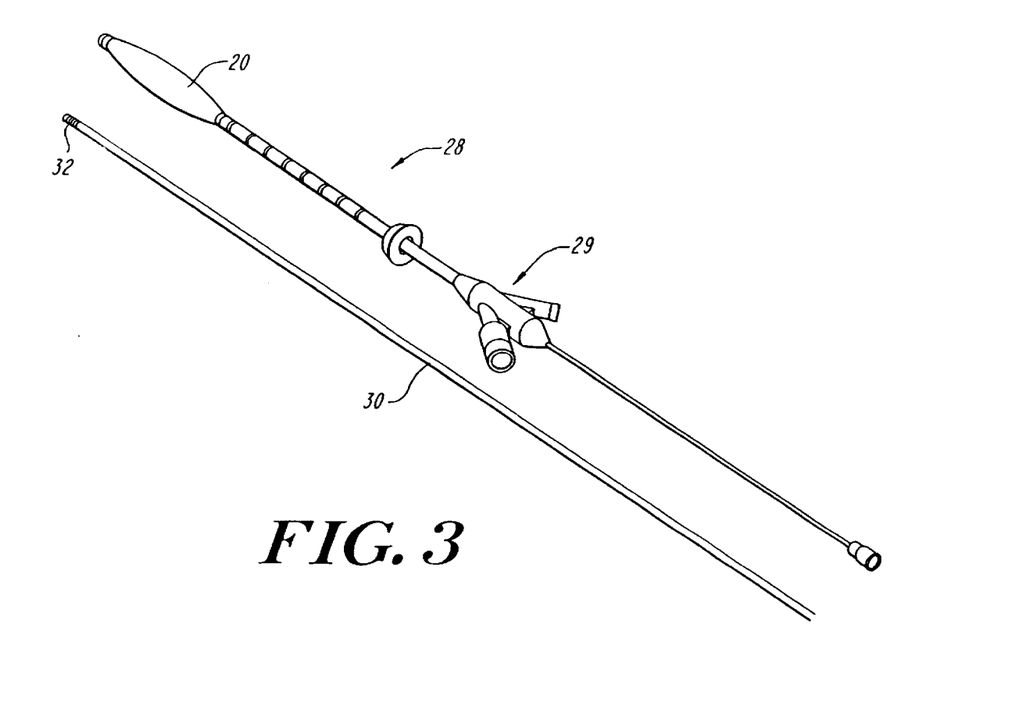
FIG. 3 is an elevational view of another device of the invention and an insertion tube for inserting into the catheter.

FIG. 3, a drug delivery catheter 28, is shown as an elevational view of the device. Membrane 20 is shown in a partially inflated position. The device includes control handle 29 for positioning of the catheter within a body cavity. In one embodiment, an inflation fluid containing a therapeutic agent is injected through a lumen or inflation port(s) (not shown) to inflate membrane 20 within a body cavity. Insertion tube 30 can be slidably positioned within a lumen of catheter 28 such that a radioactive pellet(s),e.g., seed(s), 32 irradiate the inflation fluid and therapeutic agent within membrane 20, thereby inducing a radiosensitizing or a chemotherapeutic effect on the surrounding tissue in contact with membrane 20 and the therapeutic agent exuding therefrom.

In a preferred embodiment, a distal portion of the membrane/catheter and a distal portion of the insertion tube can be detached from the main body of the catheter and insertion tube such that the detached portions remain in the body cavity for an extended period of time, e.g., 1 day to several weeks. It should be understood that the detached membrane/catheter portion retains a reservoir of inflation fluid containing a therapeutic agent, e.g., a radiosensitizer or a chemotherapeutic agent. In one embodiment, only the membrane/catheter portion and inflation fluid is left in the body cavity. In another embodiment, a portion of the insert tube is also detached, thereby allowing radioactive seeds in the lumen to continue to irradiate the therapeutic agent(s), e.g., a radiosensitizer, in the inflation fluid.

Figures 4A, 4B:
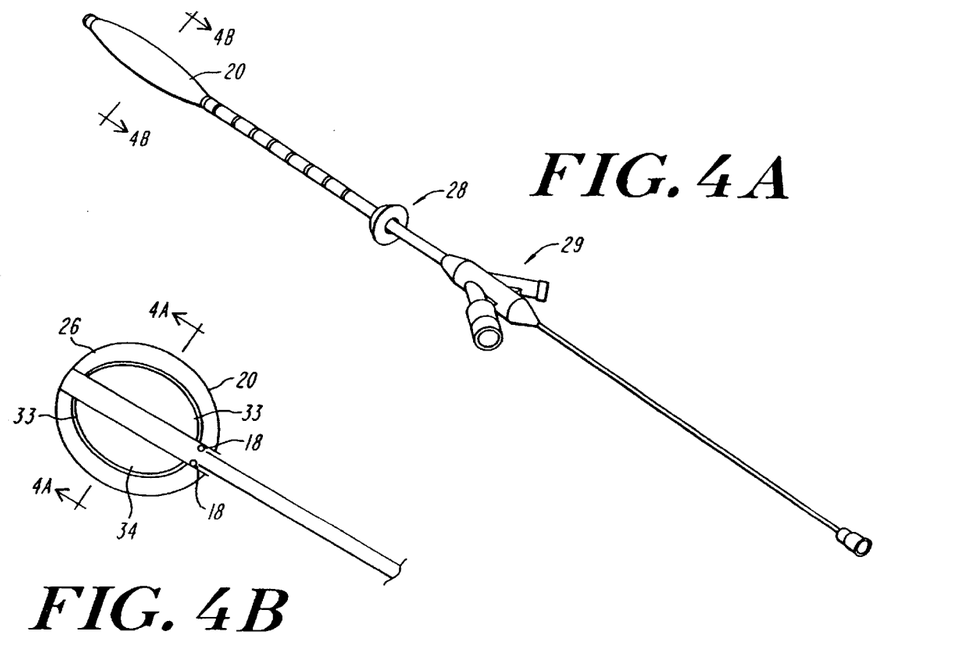
FIG. 4A is an elevation view of a double balloon device according to the invention.
FIG. 4B is a cross-sectional view of the distal portion of the device of FIG. 4A showing an inflated drug delivery membrane and an inner inflation chamber for a radioisotope.

FIG. 4A depicts another embodiment of a drug delivery catheter 28, constructed in accordance with the present invention. Membrane 20 is shown in a partially inflated position. The device includes control handle 29 for positioning of the catheter within a body cavity. As shown in FIG. 4B, an inflation fluid containing a therapeutic agent is injected through inflation ports 18 to inflate membrane 20 within a body cavity. Separately, a second membrane 33, abutting membrane 20 is inflated with a radioisotopic solution or a second inflation fluid via a lumen (not shown) or inflation ports (not shown) so that inner chamber reservoir 34 expands. The radioisotope solution produces ionizing radiation that interacts with the therapeutic agent contained within membrane 20, thereby inducing a radiosensitizing or a chemotherapeutic effect on the surrounding tissue in contact with membrane 20 and the therapeutic agent exuding therefrom. In one embodiment, the second membrane 33 does not permit passage of the radioisotope solution through the second membrane, e.g., the membrane is impermeable to fluids. Preferably, injection of inflation fluid containing a radioisotope into the second membrane 33 pressurizes the outer membrane balloon 20, such that a constant stream of first inflation fluid is delivered to the tissue.

In instances where a radioisotopic solution is not utilized in the inflation fluid in reservoir 34, the inflation fluid serves as a means to pressurize the outer inflated membrane balloon 20, thereby facilitating delivery of the first inflation fluid containing a therapeutic agent to the site for application. The second inflation fluid and second chamber 34, thereby serve to keep the outer membrane pressurized such that a constant stream of first inflation fluid is delivered to the tissue. It is to be understood that any of the devices of the invention can include a second membrane, as described above, to pressurize or maintain pressure in a first outer membrane and reservoir, thereby delivering the therapeutic agent at a constant rate, for example, in the presence of ionizing radiation supplied by an injection rod as described above. In certain embodiments, the second membrane does not allow passage of fluids into or out of the membrane, e.g., it is impermeable and can be considered a barrier.

The invention is also drawn to methods for treating aberrant cells or cancer in a body cavity. The methods include inserting a catheter including an elongated tubular body member into a body cavity, the tubular body having a proximal end, a distal end and a lumen extending therebetween, with an inflation port extending through a wall of the tubular body member in fluid communication with the lumen. An expandable membrane member is affixed to the catheter body member near the distal end and in fluid communication with at least one inflation port.

The membrane member includes a hydrophilic polymer having a redetermined permeability to migration of inflation fluid therethrough. An inflation solution containing a medicament is injected into the expandable membrane such that the medicament permeates through the membrane over a period of time treating the aberrant.

In one embodiment, the method further includes slidably positioning an insertion tube with one or more radioactive pellets, e.g., seeds, into a lumen of the catheter, such that ionizing radiation strikes the medicament, preferably a chemotherapeutic agent or a radiosensitizer, thereby treating the aberrant cells with an activated medicament.

In another embodiment, the methods include inflating a second membrane that is fixedly attached to the catheter and proximate to the first membrane with a solution containing a radioactive isotope. Preferably, the radioactive solution emits ionizing radiation that interacts with a chemotherapeutic agent or a radiosensitizer forming activated molecules useful for treating aberrant cells or cancer.

In a preferred embodiment, the distal portion of the membrane/catheter/inner chamber can be detached from the main body of the catheter such that the detached portions remain in the body cavity for an extended period of time, e.g., 1 day to several weeks. It should be understood that the detached membrane/catheter/inner chamber portion retains a reservoir of inflation fluid containing a therapeutic agent, e.g., a radiosensitizer or a chemotherapeutic agent and a solution having at least one radioisotope.

To prepare the balloon/membrane structure 20, the catheter body stock 14 and membrane 20 are bonded and when inflated by an aqueous solution containing a water soluble drug, the inflation fluid is found to permeate through the polymeric membrane with the rate of flow being governed by the composition and thickness of the membrane and the pressure differential across the polymer wall. Membrane thickness range from between about 0.01 mm to about 1 mm, preferably between about 0.05 mm to about 0.8 mm, more preferably between about 0.1 mm to about 0.5 mm.

Figure 5:
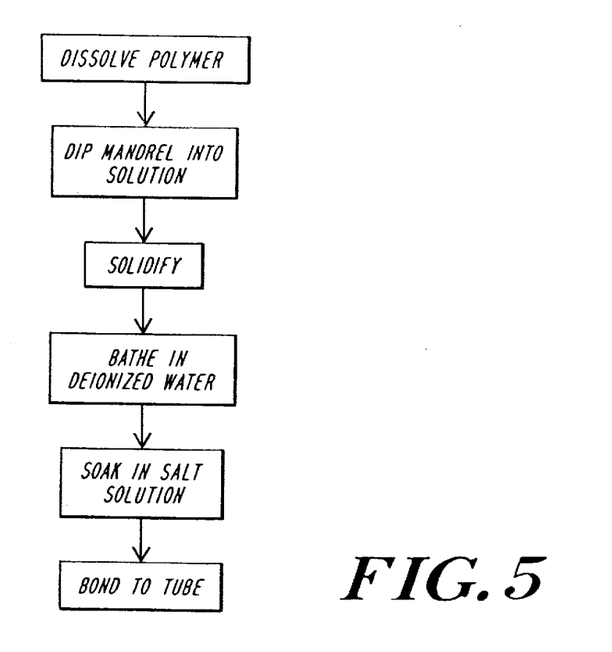
FIG. 5 shows a stepwise process for preparing a catheter device of the invention.

For example, membrane materials made of polyacrylates useful in the present invention are commercially available from SKY Polymers, Inc (Rocky Hill, N.J.). In fabricating the membranes, an acrylic acid-derived hydrophilic polymer is dissolved in a water soluble solvent to yield a final solution of 10% polymer and 90% solvent. The polymer solution can then be applied by dipping to an appropriately shaped mandrel and solidified, via water coagulation. The polymer and the mandrel can then be placed in deionized water for at least two hours until about a 95% water content is reached. The solidified polymer is then removed from the mandrel and placed into a solution of 0.9% NaCl for about 24 hours to equilibrate to a final water content of about 90% as shown in FIG. 5.

The membrane can be secured to the proximal end of the catheter by a variety of means, which are known in the art. The membrane and catheter can be formed integrally or unitarily, or may be bonded together. The membrane, in an uninflated or collapsed state, can be positioned substantially surrounding the outer proximal surface of the catheter, as is conventional for balloon catheters. Alternatively, the uninflated or collapsed membrane can be positioned within a recess at the proximal end of the catheter. The membrane can be inflated in response to a supply of fluid under pressure through the first catheter lumen, and in an inflated state extends outwardly from the recess(es) in the catheter to fill the interstitial body cavity. In the collapsed condition, the membrane can be dimensionally adapted for fitting within the interstitial cavity, and in the inflated condition can be dimensionally adapted to volumetrically substantially fill the interstitial cavity and thereby forcibly cause the tissue wall surrounding the cavity to stretch or expand. Additionally, the membrane can be dimensionally adapted to extend into the interstitial cavity a select distance and thereby contact, in the inflated condition, only a portion of the interstitial.

It is important to recognize that the hydrophilic polymer (a hydrogel) is not merely a coating layer on a permeable or impermeable membrane as known in the art as a surface treatment to enhance lubricity. In contrast, the polymeric compositions (e.g., hydrogels) of the present invention comprise the permeable membrane itself.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. All publications and references cited herein, including those in the background section, are expressly incorporated herein by reference in their entirety.

What is claimed is:

1. A drug delivery catheter comprising:
   an elongated, tubular, body member having a proximal end, a distal end and a lumen extending therebetween, and an inflation port extending through a wall of the tubular body member in fluid communication with the lumen; and
   a swellable hydrogel sheath affixed to the catheter body member near the distal end and in fluid communication with the inflation port, the hydrogel having a predetermined permeability and expandability to migration of an inflation fluid therethrough.

2. The drug delivery catheter of 1, wherein the hydrogel comprises between 50% and 98% water by weight in equilibrium.

3. The drug delivery catheter of claim 1, wherein the hydrogel can expand in one or more of x, y, or z coordinates to at least 10 times the uninflated dimension.

4. The drug delivery catheter of claim 1, wherein the hydrogel can expand in one or more of x, y, or z coordinates to at least 5 times the uninflated dimension.

5. The drug delivery catheter of claim 1, wherein the hydrogel can expand in one or more of x, y, or z coordinates to at least 2 times the uninflated dimension.

6. The drug delivery catheter of claim 1, wherein the swellable hydrogel sheath is a balloon.

7. The drug delivery catheter of claim 1, wherein the hydrogel is selected from the group consisting of polyacrylates, polymethacrylates, polyhydroxyethylacrylates, polyhydroxyethylmethacrylates, polyhydroxypropylacrylates, polyhydroxypropylmethacrylates, polyethylenes, polyvinylpyrrolidones, and polyacrylamides.

8. The drug delivery catheter of claim 7, wherein the hydrogel is crosslinked with a crosslinking agent.

9. The drug delivery catheter of claim 8, wherein the crosslinking agent is selected from the group consisting of diacrylates, triacrylates and tetra acrylates.

10. The drug delivery catheter of claim 9, wherein the crosslinked hydrogel has a crosslink density of less than 25%.

11. The drug delivery catheter of claim 9, wherein the crosslinked hydrogel has a crosslink density of less than 5%.

12. The drug delivery catheter of claim 9, wherein the crosslinked hydrogel has a crosslink density of between about 0.1% and 0.5%.

13. The drug delivery catheter of claim 9, wherein the inflation fluid is an aqueous solution containing a medicament.

* * * * *